United States Patent [19]
Chokri et al.

[11] Patent Number: 5,662,899
[45] Date of Patent: Sep. 2, 1997

[54] MACROPHAGES, PROCESS FOR PREPARING THE SAME AND THEIR USE AS ACTIVE SUBSTANCES OF PHARMACEUTICAL COMPOSITIONS

[75] Inventors: Mohamed Chokri, Deuil-la-Barre; Jacques Bartholeyns, Bures-sur-Yvette, both of France

[73] Assignee: I.D.M. Immuno-Designed Molecules, Paris, France

[21] Appl. No.: 374,629

[22] PCT Filed: May 18, 1993

[86] PCT No.: PCT/EP93/01232

§ 371 Date: Jan. 17, 1995

§ 102(e) Date: Jan. 17, 1995

[87] PCT Pub. No.: WO94/26875

PCT Pub. Date: Nov. 24, 1994

[51] Int. Cl.⁶ .......................... C12N 5/08; A61K 35/14; A61K 35/26; A61K 35/28
[52] U.S. Cl. .................. 424/93.7; 435/325; 435/347; 435/355; 435/377; 435/372; 435/373
[58] Field of Search ...................... 435/325, 347, 435/372, 373, 377, 355; 424/93.7, 93.21, 93.71

[56] References Cited

U.S. PATENT DOCUMENTS 4,963,354 10/1990 Shepard.
5,078,996 1/1992 Conlon.

FOREIGN PATENT DOCUMENTS 08800037 1/1988 Belgium.
2 657 783 8/1991 France.

OTHER PUBLICATIONS

Koeffler, Cancer Research 44: 5624–5628 1984.
Kreutz, Blood 12: 2457–2461, 1990.
Zucherman, J. heukocyte Biol 44: 187–191, 1988.
Chokri et al., "Production of Human Macrophages with Potent Antitumor Properties (MAK) by Culture of Monocytes in the Presence of GM–CSF and 1,25–Dihydroxy Vitamin D3", *Anticancer Research*, vol. 12, No. 6B, Nov. 1992, pp. 2257–2260.
Chokri et al., "Adoptive immunotherapy with bispecific antibodies: targeting through macrophages", *Research in Immunology*, vol. 143, No. 1, Jan. 1992, Paris, pp. 95–99.
Oiknine et al., "Increased susceptibility to activation and increased uptake of low density lipoprotein by cholesterol-loaded macrophages", Abstract No. 92273582.
Zimmerman et al., "Organ Specific Application of Drugs Using Cellular Capsule Systems", Chemical Abstracts, vol. 86, No. 6, Feb. 7, 1977, Columbus, Ohio, p. 294.
Andressen et al., "Adoptive Transfer of Tumor Cytotoxic Macrophages Generated in Vitro from Circulating Blood Monocytes: A New Approach to Cancer Immuotherapy", *Cancer Research*, vol. 50, 1990, Philadelphia, pp. 7450–7456.
Lopez et al., "Adoptive Immunotherapy with Activated Macrophages Grown in Vitro from Blood Monocytes in Cancer Patients: A Pilot Study", *Journal of Immunotherapy*, vol. 11, No. 3, Apr. 1992, New York, pp. 209–217.
Lopez et al. "Autologous lymphocytes prevent the death of monocytes in culture and promote, as do GM–CSF, IL–3 and M–CSF, their differentiation into macrophages", *Journal of Immunological Methods*, vol. 159, No. 1–2, Feb. 26, 1993, Amsterdam, the Netherlands, pp. 29–38.

*Primary Examiner*—Lila Feisee
*Assistant Examiner*—Nancy A. Johnson
*Attorney, Agent, or Firm*—Young & Thompson

[57] ABSTRACT

Macrophages have been developed, which possess at least one of the following properties:

- their cytotoxic activity without IFN-γ is increased by about 20 to 30% with respect to standard macrophages, and is preferably of about 70%;
- their cytotoxic activity with IFN-γ is increased by about 20 to about 40% with respect to standard macrophages, and is preferably of about 93%;
- deactivation of the cytotoxic activity following activation of IFN-γ is such that sixty hours after activation with IFN-γ, the residual cytotoxic activity is at least 30%, preferably about 55%, of the maximum cytotoxic activity presented by the macrophages due to IFN-γ activation, with said cytotoxic activity being measured as a percentage of the inhibition of 3-H thymidine incorporation by target tumoral cells, particularly U 937 cells. The macrophages are prepared by culturing healthy human monocytes and lymphocytes in a culture medium containing 1,25-dihydroxy vitamin $D_3$ and GM-CSF.

13 Claims, 1 Drawing Sheet

MACROPHAGES, PROCESS FOR PREPARING THE SAME AND THEIR USE AS ACTIVE SUBSTANCES OF PHARMACEUTICAL COMPOSITIONS

TECHNICAL FIELD

The invention relates to new macrophages, to a process for preparing the same and to their use as active substances of pharmaceutical compositions.

BACKGROUND ART

Cytotoxic leukocytes (NK, T lymphocytes, monocytes-macrophages) are potent effectors in the host defense against tumors. In vitro expansion and enhancement of the tumoricidal potential of autologous effector cells and their subsequent reinfusion into the host are currently being used in local or systemic adoptive immunotherapy (Rosenberg et al.: Progress report on the treatment of 157 patients with advanced cancer using LAK cells and IL2 or IL3 alone. N. Engl. J. Med. 316: 889, 1990; Rosenberg et al.: Use of tumor infiltrating lymphocytes and IL2 in the immunotherapy of patients with metastatic melanoma. N. Engl. J. Med. 319: 1676, 1990; Lacerna et al.: Adoptive cancer immunotherapy utilizing lymphokine activated killer cells and IFN-γ activated killer lymphocytes. Pharm. Ther. 38: 453, 1988).

Macrophages play a central role in the antitumoral response and can be activated against neoplastic cells by immunopotentiators (Adams D. and Hamilton T.: Activation of macrophages for tumor cell kill: effector mechanism and regulation. In Heppner & Fulton (eds), Macrophages and cancer. CRC Press, 1988, p. 27; Fidler L.: Macrophages and metastases. A biological approach to cancer therapy. Cancer Res. 45: 4714, 1985).

In murine models, it has been demonstrated that activated macrophages given locally in the minor inhibited minor growth and decreased metastatic development (Bartholeyns et al.: Immunotherapy of cancer: experimental approach with activated macrophages proliferating in culture. Cancer Detect. & Prev. 12: 413, 1988; Chokri et al.: Antitumoral effect of LPS, TNF, IFN and activated macrophages: synergism and tissue distribution. Anticancer Res. 9: 1185, 1989). Human monocytes isolated from blood could be differentiated in vitro into macrophages by a 7 day culture in hydrophobic bags (Chokri et al.: Antitumoral effects of LPS, TNF, IFN, and activated macrophages: synergism and tissue distribution. Anticancer Res. 9: 1185, 1989). After incubation in the presence of IFN-γ, these macrophages became activated and tumoricidal, (Macrophages activated killer= MAK) for a number of human tumors in vitro or for tumors engrafted in nude mice (Andreesen et al.: Surface phenotype analysis of human monocytes to macrophages differentiation. J. Leuk. Biol. 47; 490, 1990; Dumont et al.: Control of the antitumoral activity of human macrophages produced in large amount in view of adoptive transfer. Eur. J. Cancer 24: 1691, 1988).

Adoptive transfer of MAK has undergone phase I clinical trials by different investigators in Strasbourg, Freiburg and Paris for patients with metastatic cancer infused systematically or intraperitoneally with $10^8$ to $2\times10^9$ autologous MAK (Andreesen et al.: Adoptive transfer of, tumor cytotoxic macrophages generated in vitro from circulating monocytes: a new approach to cancer immunotherapy. Cancer Res. 50: 7450, 1990; Bartholeyns et al. Adoptive immunotherapy of solid tumors with activated macrophages: experimental and clinical results. Anticancer Res. 11: 1201, 1991; Lopez et al.: One step separation by elutriation of monocytes from leukapheresis products of cancer patients for production of IFN-γ activated macrophages in view of adoptive immunotherapy. J. Immunotherapy, 11: 209, 1992; Faradji et al.: Phase I trial of IV infusion of ex-vivo activated blood derived macrophages in patient with non small cell lung cancer: toxicity and immunomodulatory effects. Cancer Immunol. Immunother. 33: 319, 1991).

The clinical tolerance was excellent with minor side effects such as low grade fever and chills. The maximal tolerated dose could not be attained due to the limited number of MAK generated from one cytapheresis.

The recovery of larger quantities of MAK is therefore a need for optimal antitumoral efficacy in clinical trials and in therapy.

The macrophages prepared thus far in the conventional culture medium are obtained in a yield which is less than about 40%.

However, the need for macrophages presenting a higher cytotoxic activity is present in order to increase the efficacy in vivo and, subsequently, to delay the next macrophage administration.

DISCLOSURE OF THE INVENTION

One of the aims of the invention is to provide macrophages having a higher cytotoxic activity over standard macrophages.

Another aim of the invention is to provide macrophages in which the kinetics of the deactivation of the cytotoxic activity are slower with respect to standard macrophages.

Another aim of the invention is to provide a new culture medium which enables to prepare macrophages having an improved cytotoxic activity and slower deactivation kinetics of the cytotoxic activity with respect to standard macrophages.

The aims of the present invention are achieved by macrophages which have at least one of the following properties:

their cytotoxic activity without activation with IFN-γ, is increased by about 20 to 30% with respect to standard macrophages, and is preferably of about 70%;

their cytotoxic activity further to activation with IFN-γ is increased by about 20 to about 40% with respect to standard macrophages, and is preferably of about 93%;

the extension of the deactivation time of the cytotoxic activity in reply to an activation of IFN-γ, is in a ratio such that after 60 h of activation with IFN-γ, the cytotoxic activity is higher than or equal to 30%, preferably of about 55%, compared to the maximum cytotoxic activity presented by the macrophages further to an activation with IFN-γ, with said cytotoxic activity being measured as the percentage of inhibition of 3-H thymidine incorporation by target tumoral cells, particularly U 937 cells.

The expression "standard macrophages" corresponds to the ones obtained by the culture of monocytes in a standard medium, such as defined in the Example section.

The "cytotoxic activity" corresponds to the one measured as the percentage of inhibition of 3-H thymidine incorporation by target tumoral cells, particularly U937 cells, and a test for this measure is hereafter given:

Differentiated macrophages were seeded into 96-well flat microtiter plates at $10^4$ macrophages/well in 0.2 ml. After 2 h incubation at 37° C. in 5% $CO_2$ humidified atmosphere, the medium was removed and (replaced by IMDM+5% hu AB serum containing or not 250 U/ml of rhu IFNγ; plates were further incubated overnight. After washing, $10^4$ U937 tumor cells in 0.2 ml fresh medium (IMDM+10% FCS) were added to each well. After 24 h contact, 0.1 μCi of tritiated thymidine was added to each well for a further 24 h incubation.

The cells were collected and the determination of incorporated radioactivity on the fiber glass filters was carried out by β counting. The percentage inhibition of thymidine incorporation by tumor cells could be calculated according to the formula:

$$\frac{(cpmT - cpmTM)}{cpmT} \times 100$$

where cpmT=radioactivity in control tumor cells.

cpmTM=radioactivity in minor cells+macrophages mixed culture.

It is to be noted that such method enables to determine the three main types of antitumoral activity of the macrophages described in the invention, i.e.: cytolysis, cytostasis and phagocytosis.

The macrophages originate from human subjects, who can be either healthy or patients suffering from various diseases.

By way of example, standard macrophages originating from culture of monocytes from healthy subjects present a spontaneous cytotoxic activity (i.e. without activation with IFN-γ) of about 45%, versus about 70%, in the case of the macrophages of the invention; and further to IFN-γ activation, standard macrophages present a cytotoxic activity of about 76%, versus about 93%, in the case of the macrophages of the invention.

Similar enhancement of cytotoxic activity is obtained with macrophages issued from patients.

As to the kinetics of the deactivation time, Table III hereafter gathers the results relative to the measure of the activity as described above in the case of standard macrophages and of macrophages of the invention.

From the above-mentioned properties, the advantages of the macrophages of the invention appear, knowing that cytotoxic activity below 50% is useless for therapeutics.

The macrophages of the invention are such that they make a weekly treatment possible, instead of a treatment every three or four days.

According to a preferred embodiment, the macrophages of the invention have the following characteristics:

their size is from about 10 to about 20 μm;

they adhere to plastic surface;

their viability is preferably higher than about 70%;

they present a phagocytosis property;

they present on their surface antigens of differentiation, such as CD64, CD68, MAX1, HLADR;

their cytotoxic activity is higher than about 50%;

the macrophages of the invention are advantageously free of bacterial and biological contaminants.

When the size of the macrophages is higher than 20 μm, it means that they tend to fuse between one another to form giant cells, the role of which is not clearly understood; when the size is smaller than 10 μm, it means that the macrophages are not well differentiated.

The size can be measured with a channelyser (Coulter Margency-France)

The adherence property to plastic surface can be verified on Petri dishes (% adherence) after 30 minutes of incubation of the produced macrophages.

The viability is the amber of alive cells at the end of the culture, and the viability is preferably higher than about 70% and is measured by the Trypan Blue exclusion.

The phagocytosis property can be checked by ingestion of latex beads or dextran particles (30 minutes to 1 h of incubation), as described by Stevenson and Fauci, Manual of Macrophages methodology; Marcel Dekker, New York pp. 75–80, 1981.

The surface antigens of differentiation such as CD64, CD68, MAX1, HLADR are expressed at a similar or higher level with respect to standard macrophages; this can be measured by flow cytometry. Table II hereafter gives the results of phenotypes obtained under different conditions.

From this table, it can be concluded that the macrophages of the invention have new properties but the main functions of macrophages have not been altered, with the exception of the increase of the cytotoxic activity.

However, the CD71 which is the transferrin receptor is decreased in the presence of VitD$_3$+GM-CSF which correlates with an advanced activation status of the macrophages. The CD71 expression is determined as described in the Example section.

The cytotoxic activity is determined with U937 cells, the ratio between macrophages and U937 being of 1/1.

The macrophages of the invention are advantageously devoid of viral, bacterial, fungal and biological contaminants.

The invention also relates to a process for preparing macrophages as defined above, comprising the culture of monocytes in a culture medium containing 1,25-dihydroxy D$_3$ vitamin and GM-CSF.

More particularly, the process of the invention comprises the culture of both monocytes and lymphocytes in a culture medium containing 1,25-dihydroxy vitamin D$_3$ and GM-CSF for a time sufficient to obtain differentiated macrophages, preferably for about 6 or 7 days, possibly activating the macrophages resulting from the monocytes and lymphocytes with IFN-γ, and separating the macrophages from the lymphocytes, before or after the activation with IFN-γ, preferably after IFN-γ activation, and recovering the macrophages.

According to a preferred embodiment, the process of the invention comprises the following steps:

isolation of leukocytes from blood of healthy subjects or cancerous patients by cytapheresis, to obtain the cytapheresis products (i.e. concentrated leukocytes), platelet elimination, for instance by centrifugation of the cytapheresis products, to obtain a leukocyte enriched product, separation, in the leukocyte enriched products, of the mononuclear cells on one hand, and of the contaminating red blood cells and granulocytes on the other hand, culture of the mononuclear cells (monocytes+lymphocytes) in a medium containing 1,25-dihydroxy vitamin D$_3$ and GM-CSF for about 6 or 7 days, to obtain differentiated macrophages, activation of the macrophages and lymphocytes with IFN-γ for about 16 h to about 24 h, separation of the activated macrophages from the lymphocytes for instance by elutriation.

The lymphocytes can be separated from the monocytes before the culture step.

The lymphocytes can be separated from the macrophages after the culture and before the IFN-γ activation. Advantageously the macrophages and lymphocytes are separated from each other after IFN-γ activation.

In the process of the invention, D$_3$ vitamin is used at a concentration of $10^{-10}$ to about $10^{-7}$ preferably of about $10^{-8}$ M.

In the process of the invention, GM-CSF is used at a concentration of about 50 to about 1000 U/ml, particularly of about 100 to about 500 U/ml.

In the process of the invention, the culture medium is RPMI, IMDM, MEM, or DMEM.

These media are commercially available.

Advantageously, the culture medium contains indomethacin (or another cyclo-oxygenase inhibitor) or/and cimetidine (an histamine $H_2$ antogonist).

An advantageous process for prepatring the macrophages of the invention is the following:

Cytapheresis

Leukocytes from healthy subjects or from cancerous patients are isolated from peripheral blood by cytapheresis using either the Cobe 2997 or the Dideco Vivacell continous-flow blood cell separators. The cytapheresis product is centrifuged for 10 min at 280 g in order to reduce platelet contamination. The platelet-enriched plasma is removed and leukocyte pellet resuspended in a phosphate buffer solution (PBS) containing 0.1% glucose, 0.17% $PO_3HNa_2$, $2H_2O$, 0.27% $PO_3H_2Na$, 0.14% $NH_4Cl$, 0.78% NaCl (solution TS745 laboratoire Bruneau, France).

The enriched leukocyte pellet is obtained with an average of 7 to $9 \times 10^9$ leukocytes (50% of mononuclear cells).

Isolation of mononuclear cells

Human mononuclear cells are separated from red blood cells and from contaminating granulocytes, by 15 min centrifugation at 1000 g on a COBE 2991 or Stericell cell processor using Ficoll Paque of density 1.077 (Pharmacia). After 3 washings in phosphate buffered saline solution without calcium and magnesium, the monocytes are obtained with about 50% purity as shown by channelyser analysis (Coulter Margency-France).

Culture

Differentiated human macrophages are obtained by 7 days in culture of monoclear cells in hydrophobic bags in Teflon or polypropylene (Dupont-J. BIO, life cell-Travenol stericell-TERUMO) at 37° C. and 5% $CO_2$, 95% humidified atmosphere. Total mononuclear cells are seeded at $5.10^6$ cells/ml in Iscove modified medium (IMDM, Gibco) or equivalent medium supplemented by penicillin (100 UI/ml), streptomycine (100 μg/ml), L-glutamine (2 mM, Gibco), pyruvic acid (2 mM, Gibco), Indomethacin ($5.10^6$M, Sigma), cimetidine ($10^{-6}$ to $10^{-5}$M), mercaptoethanol ($3.10^{-5}$M, Gibco) non essential amino-acids (1%, Gibco) and 2–5% of autologous or AB serum. The addition of GM-CSF (500 U/ml, Shering) and/or 1,25 dihydroxy-VitD$_3$ (cholecalciferol $10^8$M, Roche, Basel, Sw) was done in comparative experiment.

Activation of macrophage to cytotoxicity was performed by a further 16–18 h culture in presence of 250 U/ml of IFN-γ (Boehringer, Ingelheim, FRG).

Elutriation

The differentiated macrophages-obtained aver 7 days of culture and after activation are centrifuged at 550 g for 10 min and the pellet is resuspended in phosphate buffered saline solution containing 0.1% glucose, 0.17% $PO_3HNa_2$, $2H_2O$, 0.27% $PO_3H_2Na$, 0.14% $NH_4Cl$, 0.78% NaCl (solution TS745 laboratoire Bruneau, France) with 2% human serum albumin (HSA, CNTS-France).

The cells are then subjected to elutriation using a Beckman J6 ME centrifuge equipped with a J5.O rotor and a 40 ml elutriation chamber as described by Andreesen et al. (Cancer Res., 50, 1990).

The differentiated macrophages are collected at a constant rotor speed and increasing the flow rate.

The process of the invention enables to obtain a yield of macrophages higher than about 40%, and preferably of about 76%, with said yield being the ratio between the obtained live macrophages and the starting monocytes. This yield can be determined by cell counting and channelyser.

According to a preferred embodiment, the process of the invention is such that killed tumoral cells are added into the culture medium simultaneously with monocytes, both cells coming preferably from the same patient, preferably at the ratio of about 1 million of killed tumoral cells/ml, with said killed tumoral cells being processed at the same time as macrophages.

The killed tumoral cells can then be processed simultaneously with the leukocytes, in an mount of about $1 \times 10^6$ ml, and can be separated from the macrophages for instance at the same time as the lymphocytes, after IFN-γ activation or before IFN-γ activation, and preferably after IFN-γ activation.

This process allows to obtain macrophages and lymphocytes specific for the tumor, killing very efficiently in vivo these specific tumor cells.

The invention also relates to the macrophages liable to be obtained according to the above-defined process.

The invention also relates to pharmaceutical composition containing, as active substance, macrophages as defined above.

The invention also relates to a medium containing elements necessary for the growth and differentiation of monocytes into macrophages of the invention, and in addition containing $D_3$ vitamin and GM-CSF.

The macrophages of the invention can be part of a kit containing:

means for the recovery of lymphocytes and monocytes free of contaminants;

appropriate buffer and wash solutions, and possibly appropriate means for the conservation of macrophages;

means for preparing a culture medium for the monocytes and possibly the lymphocytes and containing 1,25-dihydroxy vitamin $D_3$ and GM-CSF;

possibly IFN-γ.

According to an advantageous embodiment of the invention, the kit contains:

means for recovering and centrifuging blood to obtain a leukocyte concentrate;

means for separating lymphocytes and monocytes from the other white cells and for eliminating the contaminating red cells;

culture medium for macrophages and possibly lymphocytes with complements and particularly 1,25-dihydroxy vitamin D3 and GM-CSF and possibly indomethacin and/or cimetidine;

means for the separation of lymphocytes from macrophages;

appropriate means for the conservation of macrophages;

appropriate buffer and wash solutions;

possibly IFN-γ.

By way of examples, an advantageous kit comprises the following elements:

1—Cytapheresis kit (Fenwal),

2—Transfer bag (R 20-21-Fenwal),

3—Kit of centrifugation under Ficoll gradient (Gradient/wash processor set Stericell-Terumo) or blood cell processor (Cobe 912-647-819), 4—Elutriation Kit (Macopharma), 5—Transfert Pack Unit 2L (Travenol—4R2041), 6—Hydrophobic bag for cell culture (Teflon, J. BIO-lifecell, Travenol-Stericell, Terumo), 7—Injection bag (Travenol), 8—Phosphate buffered saline solution (solution TS745 Laboratories Bruneau), 9—Ficoll-Paque (Pharmacia), 10—Human Albumin solution (Biotransfusion), 11—Culture medium (IMDM-Gibco), 12—Penicillin/Streptomycine (Gibco), 13—L-Glutamine (Gibco), 14—Non essential amino-acids (Gibco), 15—Pyruvic acid (Gibco), 16—Indomethacin (Sigma), 17—Mercaptoethanol (Gibco), 18—GM-CSF (Shering), 19—1,25 dihydroxy-Vit $D_3$ (Roche, Basel, Sw), 20—Vial of IFN-$\gamma$ (Boehringer).

The invention also relates to products containing macrophages according to the invention, and lymphocytes, as a combined preparation for simultaneous, separate or sequential use in adoptive immunotherapy.

According to an advantageous embodiment, the products of the invention as defined above are characterised in that they contain the macrophages and the lymphocytes in a ratio of at least $\frac{1}{3}$–$\frac{2}{3}$ expressed in cell number.

In this embodiment, the macrophages and the lymphocytes are both injected to a patient. This can mean that:

either the elutriation step is cancelled and the macrophages and lymphocytes are injected
after IFN-$\gamma$ activation;
or after simultaneous IFN-$\gamma$ and IL-2 activation;

or the macrophages are separated from each other after the culture, but before activation, with macrophages being subsequently activated with IFN-$\gamma$ and lymphocytes being subsequently activated with IL-2.

The invention also relates to bispecific antibodies liable to recognize an antigen of a macrophage of the invention and an antigen of a tumoral cell which is to be targetted by said macrophage.

The bispecific antibodies can be prepared as described in Chokri et al. Res. Immunol. 143 (1992).

The bispecific antibodies can be injected at the same time as the macrophages of the invention, or can be pre-incubated with macrophages before injection.

The invention also relates to a method for the treatment of cancer, comprising the administration of an appropriate mount of macrophages according to the invention, and preferably in an mount of about $2\times10^9$ to about $5\times10^9$ macrophages.

A method according to the invention for the treatment of cancer comprises the administration of lymphocytes in an amount of about $4\times10^9$ to about $10\times10^9$ lymphocytes.

The macrophages of the invention can also be used as nucleic acid and/or drug vectors. The invention thus comprises macrophages containing exogenous nucleic acids and/or drugs.

Regarding macrophages containing exogenous nucleic acids, the macrophages are prepared. By transfection, DNA coding for a cytokine or for a defective protein, or for a tumor antigen, is integrated into the macrophages and it is checked that it is expressed on the macrophages before injecting it into the patient.

The long survival of the macrophages allows the in vivo expression of the integrated protein genes.

Figure 1:
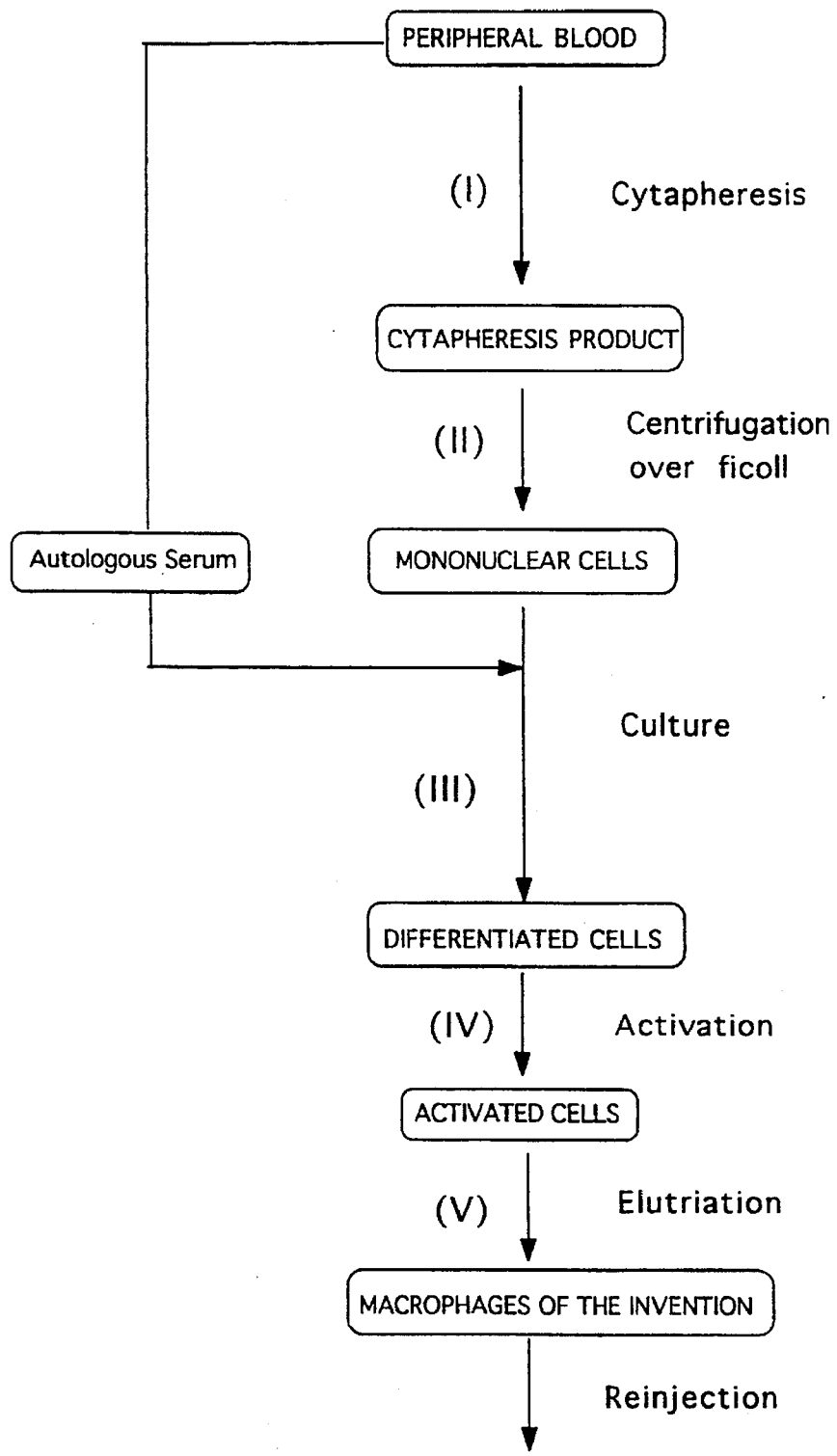
FIG. 1 represents a schematic diagram of the production of the macrophages of the invention.

Peripheral blood taken from a healthy subject or from a patient is submitted to cytapheresis (I), which enables to obtain cytapheresis product.

Said cytapheresis product is centrifuged on Ficoll and washed (II) to yield mononuclear cells (monocytes+lymphocytes).

Said mononuclear cells are cultured (III) in an appropriate medium as defined herein, and containing autologous serum from the healthy subject or from the patient.

The culture of the mononuclear cells gives a cellular suspension which is activated (IV) and further to the activation, a step of elutriation (V) is carried out, which enables to obtain the macrophages of the invention, which are then reinjected to the patient or to the healthy subject.

The materials used for each of the steps can be the following:

| | |
|---|---|
| (I) | cytapheresis bag, |
| | ACD solution, |
| | calciparine, |
| | buffered saline solution, |
| (II) | blood cell processor-processing set, |
| | Ficoll-Paque, |
| | transfer bag, |
| (III) | culture bag |
| | Iscove modified Dulbecco medium, |
| | L-Glutamine, |
| | non essential amino acids, |
| | pyruvic acid, |
| | GM-CSF, |
| | dihydroxyvitamin $D_3$, |
| | $\beta$- mercaptoethanol, |
| | streptomycin, |
| | indomethacine, |
| | $CO_2$, |
| (IV) | interferon-$\gamma$, |
| (V) | human albumin solution, |
| | injection bag. |

EXAMPLE

I) Materials and Methods

Isolation of mononuclear cells. Leukocytes from normal thrombocyte subjects were isolated from peripheral blood cytapheresis (using the COBE 2997 or Dideco Vivacell continuous cell separator). After collection of platelets for transfusion purposes, the concentrated leukocyte apheresis residue was resuspended. Human mononuclear cells were collected by 15 minutes centrifugation at 1000 g on a COBE 2921 cell processor using Ficoll Paque of density 1.077 (Pharmacia). After 3 washings in phosphate buffered saline without calcium and magnesium, mononuclear cells were obtained with 30 to 50% monocytes as shown by channelyser analysis (Coulter Margency-France).

Culture. Differentiated human macrophages were obtained by a 7 day culture of mononuclear cells in Teflon bags (Dupont-J. BIO, Les Ulis) at 37° C. and 5% $CO_2$, 95% humidified atmosphere. Total mononuclear cells were seeded at $5.10^6$ cell/ml in Iscove modified Dulbecco medium (IMDM, Gibco) supplemented with penicillin (100 u.i./ml, streptomycin (100 μ/ml), L-glutamine (2 mM, Gibco), pyruvic acid (2 mM. Gibco), Indomethacin ($5.10^{-6}$M, Sigma), mercaptoethanol ($3.10^{-5}$M. Gibco), non essential amino-acids (2%. Gibco) and 5% AB serum. It is to be noted that this medium is defined as standard medium.

enabling to obtain "standard macrophages", as already mentioned above. The addition of GM-CSF (500 U/ml, Behring) and/or 1,25 dihydroxy-Vit $D_3$ (cholecalciferol $10^{-8}M$, Roche, Basel, Sw) was done in a comparative experiment. Activation of the macrophages to cytotoxicity was performed by a further 18 h culture in the presence of 250 U/ml of IFN-γ (Boehringer, Ingelheim, FRG). The culture medium as well as the cell preparations contained less than 0.02 i.U. LPS per ml.

Elutriation. The mononuclear cells or the differentiated macrophages obtained after 7 day culture and activation were centrifuged at 550 g and the pellet was resuspended in phosphate buffered saline solution containing 0.1% glucose, 0.17% $PO_3HNa_2$, $2H_2O$, 0.27% $PO_3H_2Na$, 0.14% $NH_4Cl$, 0.7% NaCl (solution TS745 Laboratoire Bruneau, 92, France) with 2% human serum albumin (HSA, CNTS-France). The cells were then subjected to elutriation as previously described by Lopez et al (one step separation by elutrition of monocytes from leukapheresis products of cancer patients for production of IFN-γ, activated macrophages in view of adoptice immunotherapy. J. Immunotherapy, 11: 209, 1992). The elutriation method used for differentiated macrophages collected as a "rotor off" fraction was the one described by Andreesen (Andreesen et al., Adoptive transfer of tumor cytotoxic macrophages generated in vitro from circulating monocytes: a new approach to cancer immunotherapy. Cancer Res. 50: 7450, 1990) at a constant rotor speed and increasing flow rate.

Flow cytometry. Phenotype analysis of macrophage populations was done by flow cytometry using murine monoclonal antibodies directed against membrane proteins and revealed by FITC conjugates. The a-CD3 CD14, CD71antibodies were from DAKO (Versailles, France), anti-HLADR from COULTER (Margency, France), anti CD64 (CNTS, France) and Max-1 antibody recognizing a membrane antigen of differentiated macrophages (Andreesen et al., Surface phenotype analysis of human monocytes to macrophages differentiation. J. Leuk. Biol. 47: 490, 1990) was a gift of Dr. Emmrich (Erlangen, Germany). Briefly:$5.10^5$ to $10^6$ cells in 0.2% of bovine serum albumin in phosphate buffered saline were incubated on ice for 30 min in the presence of FITC labelled or unlabelled monoclonal antibodies or the isotype immunoglubulin controls. For indirect immunofluorenscense, after washing, the cells were further exposed to FITC conjugated F (ab')2 goat anti murine IgG (Immunotech.) for 25 minutes on ice. The cells were analysed after washing by flow cytometry (EPICS Profile, Coulter). The acquisition gate was set around the major population of large cells.

Tumor targets. The human histiocytic cell line U937 was maintained in suspension as a continuous line cultured in MDM with 10% fetal calf serum (FCS, Gibco) and used during exponential growth as target in the cytotoxicity assay.

In vitro antitumoral assay. Differentiated macrophages were seeded into 96-well flat microtiter plates at $10^4$ macrophages/well in 0.2 ml. After 2 h incubation at 37° C. in 5% $CO_2$ humidified atmosphere, the medium was removed and replaced by IMDM+5% hu AB serum containing or not 250 U/ml of rhu IFN-γ; plates were further incubated for one night. After washing, $10^4$ U937 tumor cells in 0.2 ml fresh medium (IMDM+10% FCS) were added to each well. After 24 h contact, 0.1 µCi of tritiated thymidine was added for a further 24 h incubation to each well.

The cells were collected and the determination of incorporated radioactivity on the fiber glass filters was carried out by β counting. The % inhibition of thymidine incorporation by tumor cells was calculated according the formula:

$$\frac{(cpmT - cpmTM)}{cpmT} \times 100$$

where cpmT=radioactivity in control minor cells, cpmTM=radioactivity in tumor cells+macrophages mixed culture.

II) Results

Recovery of large cells with macrophage morphology after 7 day differentiation of mononuclear cells. The recovery of the mononuclear cells after one week of culture was not markedly modified by the addition of GM-CSF or $(OH)_2$ $VitD_3$. In contrast, the mount of large cells with macrophage morphology was markedly enhanced in presence of GM-CSF (Table I). The addition of GM-CSF increased significantly ($p<0.001$) the macrophage recovery (result of 12 different cultures). The addition of $(OH)_2$ Vit $D_3$ to the culture did not enhance the amount of macrophages; however, the combination of GM-CSF+Vit $D_3$ allowed a reproducible high yield of macrophages (Table I).

Table I gathers the results obtained regarding the yield and the cytotoxic activity; the last column corresponds to macrophages of the invention.

TABLE I

Mean recovery and antitumoral potency of MAK produced under different conditions.

| MAK | Standard medium | + VitD3 | + GM-CSF | + VitD3 + GM − CSF |
|---|---|---|---|---|
| (a) yield after 7 days | 37 ± 7 | 36 ± 7 | 69 ± 10* | 76 ± 11* |
| (b) cytotoxic activity: | | | | |
| −IFN − γ | 45 ± 9 | 59 ± 14 | 44 ± 5 | 71 ± 5* |
| +IFN − γ | 76 ± 5 | 76 ± 7 | 76 ± 5 | 93 ± 2* |

(a) % of macrophages to the number of monocytes seeded and standard error of 12 determinations.
(b) % inhibition of 3H-thymidine incorporation by U937 cells, mean and standard error of 8 different preparations with 5 determinations in each case: *<0.05 by student t text comparing values in standard medium.

Phenotype of MAK produced in the presence or absence of GM-CSF and of $(OH)_2VitD_3$. Mononuclear cells were fully differentiated into macrophages after 7 days of culture and activation with IFN-γ, as shown by major expression of specific differentiation antigens (Max-1, CD64, HLA-DR) (Table II). No change in the phenotypes of the antigen was observed, except for the expression of the transferrin receptor (CD71) which was decreased in the presence of GM-CSF or of GM-CSF+$(OH)_2$Vit $D_3$ ($p<0.05$). This decrease Of CD71 was observed in association with large differentiated cells. Control non relevant Ig used for direct and indirect fluorescence labelled respectively less than 5% and less than 10% of the large cells.

Table II hereafter gathers the results concerning the phenotype of macrophages obtained under various conditions; the last column corresponds to the macrophages of the invention.

TABLE II

Phenotype of MAK produced under various conditions.

|  | Standard | +GM − CSF | +VitD3 | GM − CSF + VitD3 |
|---|---|---|---|---|
| CD3 | 25 ± 8 | 13 ± 4 | 19 ± 7 | 17 ± 2 |
| CD14 | 91 ± 6 | 95 ± 6 | 85 ± 10 | 93 ± 11 |
| CD71 | 83 ± 11 | 59 ± 22 | 81 ± 16 | 46 ± 17 |
| HLA-DR | 94 ± 3 | 96 ± 2 | 94 ± 4 | 95 ± 1 |
| MAX-1 | 89 ± 9 | 84 ± 6 | 89 ± 10 | 79 ± 7 |
| CD64 (FCγRI) | 95 ± 4 | 96 ± 4 | 96 ± 4 | 98 ± 1 |

Values are means and standard errors of 5 different experiments.

Functionality of macrophages: antitumoral activity. Macrophages differentiated in culture did not express high spontaneous antitumoral activity if not exposed to IFN-γ, except for the macrophages produced in the presence of $(OH)_2Vit\ D_3$+GM-CSF which spontaneously inhibited the proliferation of U937 cells. After 18 h activation with IFN-γ, MAK cells became antitumoral in vitro under the different culture conditions. The higher antitumoral activity was achieved more reproducibly for macrophages differentiated in the presence of $VitD_3$+GM-CSF (Table III).

Kinetics of macrophage activation by INF-γ. Macrophages differentiated under standard conditions were activated for antitumoral functions after 18 h contact with 250 U/ml of IFN-γ; this antitumor activity then decreased slowly over time to reach control values after 3 to 4 days. These macrophages could be fully reactivated to high antitumor activity by re-exposure to 250 U/ml IFN-γ.

Macrophages differentiated in the presence of GM-CSF+ $(OH)_2\ VitD_3$ presented a higher antitumoral activity than the control; after activation with 250 U/ml INF-γ they maintained this antitumoral activity at a high level, even after 2 to 3 days in culture. Indeed, 60 h after activation the inhibition of thymidine incorporation by U937 tumor cells was 28±3% for macrophages compared to 54±2% for macrophages exposed to GM-CSF and $(OH)_2\ VitD_3$ (p<0.01 mean of 3 experiments). A new exposure of these cultured macrophages to 250 U/ml rh INF-γ increased the antitumor potency to more than 80% inhibition of thymidine uptake by U937 cells at 1/1 effector/tumor ratio (mean of 3 different experiments).

Table III hereafter gathers the results relative to kinetics, and compares standard macrophages and macrophages of the invention.

Kinetics of macrophages deactivation after IFN-γ exposure for 18 h.

| Time after IFN-γ activation (h) | % inhibition of 3-H Thymidine incorporation by U937 | |
|---|---|---|
|  | standard macrophages | macrophages of the invention |
| 0 | 17 ± 2 | 43 ± 3 |
| 18 | 55 ± 5 | 73 ± 3 |
| 40 | 31 ± 7 | 53 ± 2 |
| 65 | 28 ± 3 | 54 ± 2 |

The results given are the means of 3 experiments.
In this table:
at time 0, there is no INF-γ activation;
time 18:18 h after the start of INF-γ activation, which corresponds to the end of activation; macrophages are no longer in the presence of IFN-γ;
time 40:40 h after the start of INF-γ activation;
time 65:65 h after the start of INF-γ activation.

It is to be noted that the maximum of cytotoxic activity is obtained further to an activation with INF-γ lasting between about 16 h and about 24 h.

We claim:

1. Macrophages having at least one of the following properties:
   their cytotoxic activity without IFN-γ is increased by about 20 to 30% with respect to standard macrophages;
   their cytotoxic activity with IFN-γ is increased by about 20 to about 40% with respect to standard macrophages;
   deactivation of the cytotoxic activity following activation of IFN-γ is such that sixty hours after activation with IFN-γ, the residual cytotoxic activity is at least 30% of the maximum cytotoxic activity presented by the macrophages due to IFN-γ activation, with said cytotoxic activity being measured as a percentage of the inhibition of 3-H thymidine incorporation by target tumoral cells, particularly U 937 cells;
   said macrophages being prepared by culturing healthy human monocytes and lymphocytes in a culture medium containing 1,25-dihydroxy vitamin $D_3$ and GM-CSF.

2. Macrophages according to claim 1, having the following characteristics:
   their size is from about 10 to about 20 μm;
   they adhere to plastic surface;
   their viability is higher than about 70%;
   they present a phagocytosis property;
   they present on their surface antigens of differentiation selected from the group consisting of CD64, CD68, MAX1, and HLADR;
   their cytotoxic activity is higher than about 50%.

3. Process for preparing macrophages according to claim 1, comprising culturing monocytes in a culture medium containing 1,25-dihydroxy $D_3$ vitamin and GM-CSF.

4. Process according to claim 3 comprising culturing both monocytes and lymphocytes in a culture medium containing 1,25-dihydroxy vitamin $D_3$ and GM-CSF for a time sufficient to obtain differentiated macrophages, activating the macrophages resulting from the monocytes and lymphocytes with IFN-γ, and separating the macrophages from the lymphocytes, before or after the activation with IFN-γ, and recovering the macrophages.

5. Process according to claim 3, wherein $D_3$ vitamin is used at a concentration of $10^{-10}$ to about $10^{-7}$.

6. Process according to claim 3, wherein GM-CSF is used at a concentration of about 50 to about 1000 U/ml.

7. Process according to claim 3, wherein the culture medium is RPMI, IMDM, MEM, or DMEM.

8. Process according to claim 3, wherein the culture medium contains indomethacin or/and cimetidine.

9. Process according to claim 3, wherein the yield of macrophages is from about 40% to 76%.

10. Process according to claim 3, wherein killed tumoral cells are added into the culture medium simultaneously with macrophages, both cells coming from the same patient, at the ratio of about 1 million of killed tumoral cells/ml, with said tumoral cells being processed at the same time as macrophages.

11. Pharmaceutical compositions containing, as active substance macrophages according to claim 1.

12. Method for the treatment of cancer, comprising the administration of macrophages according to claim 1 in an amount from about $2 \times 10^9$ to $5 \times 10^9$ macrophages.

13. Method according to claim 12 for the treatment of cancer, comprising the administration of lymphocytes in an amount of about $4 \times 10^9$ to about $10 \times 10^9$ lymphocytes.

* * * * *